United States Patent [19]

Kuroda et al.

[11] Patent Number: 5,223,637

[45] Date of Patent: Jun. 29, 1993

[54] KS-506 COMPOUNDS

[75] Inventors: Kazutoshi Kuroda, Machida; Hiroshi Kase, Koganei; Katsuhiko Ando, Machida; Isao Kawamoto, Hiratsuka; Toru Yasuzawa, Yokohama; Hiroshi Sano, Machida; Joji Goto, Machida; Koji Yamada, Machida, all of Japan

[73] Assignee: Kyowa Hakko Kogyo Co., Ltd., Tokyo, Japan

[21] Appl. No.: 889,388

[22] Filed: May 28, 1992

Related U.S. Application Data

[62] Division of Ser. No. 329,329, Mar. 27, 1989, Pat. No. 5,142,096.

[30] Foreign Application Priority Data

| Mar. 31, 1988 | [JP] | Japan | 63-80084 |
| Mar. 31, 1988 | [JP] | Japan | 63-80085 |
| Aug. 30, 1988 | [JP] | Japan | 63-216044 |

[51] Int. Cl.$^5$ .............. C07C 307/16; C07C 69/612; C07C 69/90; A61K 35/74
[52] U.S. Cl. ................... 558/253; 558/255; 560/61; 560/62; 560/67; 560/70; 560/72; 560/66
[58] Field of Search ............ 560/66, 61, 62; 558/253, 255

[56] References Cited

U.S. PATENT DOCUMENTS

| 3,190,824 | 6/1965 | Taub et al. | 560/72 |
| 3,884,960 | 5/1975 | Spivack et al. | 560/72 |
| 4,204,071 | 5/1980 | Anderson et al. | 558/253 |
| 4,555,402 | 11/1985 | Matsuda et al. | 424/122 |

FOREIGN PATENT DOCUMENTS

| 61-176531 | 8/1986 | Japan | 560/66 |
| 62-215551 | 9/1987 | Japan | 560/66 |
| 39225 | 2/1988 | Japan. | |

OTHER PUBLICATIONS

Tereferol-J. Antibiot. 37, 6-9 (1984) Nakagawa et al. I.
Griseolic acid-J. Antibiot. 38, 823 (1985) Nakagawa et al. II.
Reticurol-J. Antibiot. 28, 558-560 (1975) Furutani et al.
PDE-I, II-Agr. Biol. Chem. 42, 1331-1336 (1978) Enomoto et al.
KS-619-1-J. Antibiot. 40, 1104-1110 (1987) Matsuda et al. I.
K-259-2-J. Antibiot. 40, 1092-1100 (1987) Matsuda et al. II.
Genistein-Agr. Biol. Chem. 51, 3003-3009 (1987) Matsuda et al. III.
Elix, et al "Five New Fully Substituted Depsides from the Lichen" pp. 2023-2029; (1987) Aust J. Chem., vol. 40.
Chemical Abstracts, vol. 108; p. 434 (1968).

Primary Examiner—Floyd D. Higel
Attorney, Agent, or Firm—Antonelli, Terry, Stout & Kraus

[57] ABSTRACT

KS-506a, KS-506x and KS-506g having an activity to inhibit cyclic nucleotide phosphodiesterase and KS-506m and KS-506h having an activity to inhibit histamine release are produced by culturing a microorganism belonging to the genus Mortierella.

1 Claim, No Drawings

KS-506 COMPOUNDS

This application is a divisional application of application Ser. No. 329,329 filed Mar. 27, 1989, now U.S. Pat. No. 5,142,096.

BACKGROUND OF THE INVENTION

The present invention relates to novel physiologically active substances, herein identified as KS-506a, KS-506x, KS-506g, KS-506m and KS-506h, and a process for the production thereof.

KS-506a, KS-506x and KS-506g have an activity to inhibit cyclic nucleotide phosphodiesterase and are useful as pharmaceuticals such as bronchodilators, cardiotonics, vasodilators, hormone secretomotor agents and antiallergic agents and also as reagents for the research of cyclic adenosine-3',5'-monophosphoric acid (hereinafter referred to as cAMP) and cyclic guanosine-3',5'-monophosphoric acid (hereinafter referred to as cGMP).

KS-506m and KS-506h have an activity to inhibit histamine release and are useful as pharmaceuticals such as antiallergic agents and antiinflammatory agents.

cAMP and cGMP are substances which play an important role as a second messenger in the signal transduction system in a living body. It is generally considered that they are involved in contraction of smooth muscles of bronchus and blood vessel, contraction of cardiac muscle, secretion of hormone, release of transmitters such as histamine, platelet aggregation, cell growth and differentiation, and the like. Cyclic nucleotide phosphodiesterase (hereinafter referred to as PDE) is an enzyme which hydrolyzes cAMP and cGMP to form adenosine-5'-monophosphoric acid and guanosine-5'-monophosphoric acid, respectively. It has been known that substances inhibiting the enzyme raise the concentration of cAMP and cGMP in a living body and as a result exhibit a bronchodilator action, a smooth muscle-relaxing action, a cardiotonic action, a hormone secretomotor action, an action of inhibiting the release of transmitters such as histamine which is one of the causative substances of allergy, an antithrombotic action, etc.

Heretofore, the following substances have been known as substances which are produced by microorganisms and have a PDE-inhibiting action:

(1) Terferol

J. Antibiot. 37, 6-9 (1984)

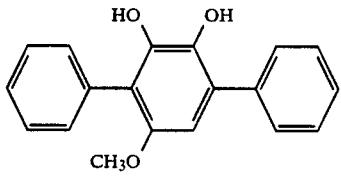

(2) Griseolic acid

J. Antibiot. 38, 823 (1985)

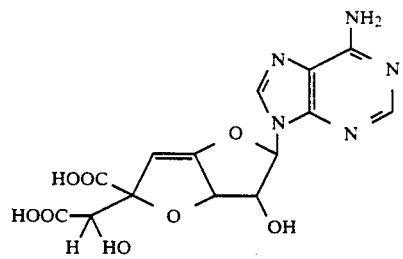

(3) Reticurol

J. Antibiot. 28, 558-560 (1975)

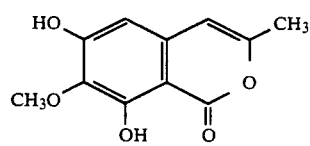

(4) PDE-I, II

Agr. Biol. Chem. 42, 1331-1336 (1978)

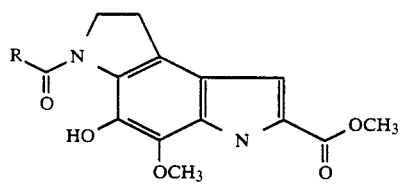

PDE-I: R=—NH$_2$
PDE-II: R=—CH$_3$ (5) KS-619-1

J. Antibiot. 40, 1104-1110 (1987)

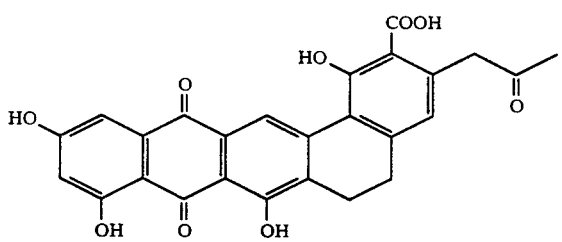

(6) K-259-2

J. Antibiot. 40, 1092-1100 (1987)

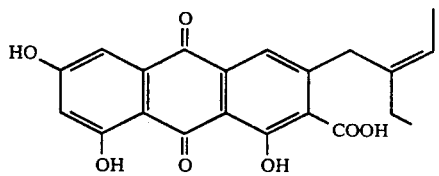

(7) Genistein

Agr. Biol. Chem. 51, 3003-3009 (1987)

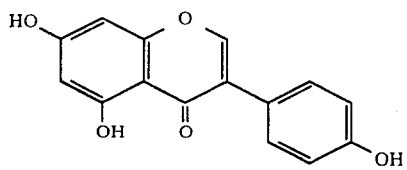

Substances (1) to (5), substance (6) and substance (7) are produced by actinomycetes of the genus Streptomyces, the genus Micromonospora and the genus Streptosporangium, respectively. Further, TPI having the following structure has been known as a substance which is produced by a fungus and inhibits PDE:

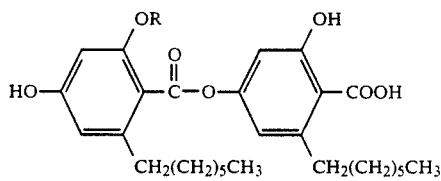

TPI-1: R = β-D-glucopyranosyl
TPI-2: R = β-D-galactopyranosyl
TPI-3: R = 6'-O-acetyl-β-D-glucopyranosyl
TPI-4: R = 6'-O-acetyl-β-D-galactopyranosyl
TPI-5: R = H (Japanese Published Unexamined Patent Application No. 215551/1987)

Furthermore, KS-503c which is produced by a microorganism belonging to the genus Hormonema and has a PDE-inhibiting activity has been disclosed in Japanese Patent Application No. 39225/1988.

As chemically synthesized substances, there have been known theophylline, papaverine and the like used as pharmaceuticals such as cardiotonics and vasodilators.

As compounds which are produced by microorganisms and have an activity to inhibit histamine release, there have been known K-252 (U.S. Pat. No. 4,555,402) and KT 5556 (Japanese Published Unexamined Patent Application No. 176531/1986) produced by microorganisms belonging to the genus Nocardiopsis.

SUMMARY OF THE INVENTION

The present invention provides novel compounds KS-506a, KS-506x, KS-506g, KS-506m and KS-506h, which are herein generically referred to as KS-506 compounds.

KS-506a, KS-506x and KS-506g have an activity to inhibit PDE and are useful as pharmaceuticals such as bronchodilators, cardiotonics, vasodilators, hormone secretomotor agents and antiallergic agents and also as reagents for the research of cAMP and cGMP.

KS-506m and KS-506h have an activity to inhibit histamine release and are useful as pharmaceuticals such as antiallergic agents and antiinflammatory agents.

KS-506 compounds can be prepared by culturing microorganisms belonging to the genus Mortierella and being capable of producing the compounds in a culture medium.

DETAILED DESCRIPTION OF THE INVENTION

KS-506a, KS-506x and KS-506g are represented by the following general formula:

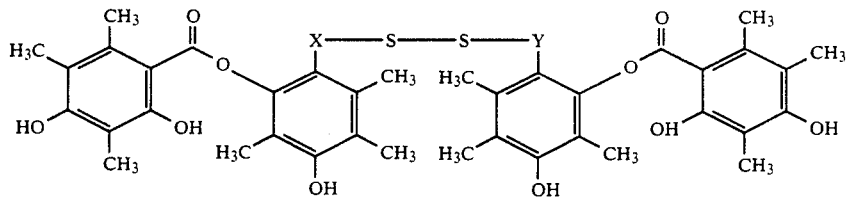

KS-506a:

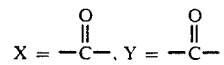

KS-506x:

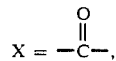

Y = single bond
KS-506g: X = single bond, Y = single bond
KS-506m and KS-506h are represented by the following general formula:

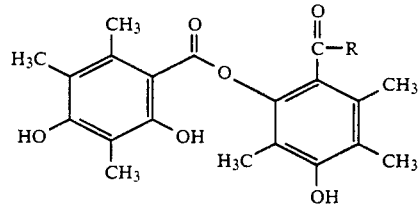

KS-506m:

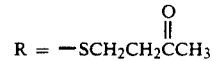

KS-506h: R = —OCH₃

The physicochemical properties of KS-506a, KS-506x, KS-506g, KS-506m and KS-506h are as follows.
1. KS-506a
  (1) Appearance: white powder
  (2) Molecular formula: $C_{40}H_{42}O_{12}S_2$
  (3) Infrared absorption spectrum: (the solution method, in CHCl₃) cm⁻¹: 3630, 3400, 1707, 1655, 1615, 1587, 1460, 1425, 1310, 1167, 1104
  (4) ¹H-NMR spectrum: (400 MHz, in CDCl₃) δ(ppm): 11.36(2H, s), 5.32(2H, br s), 5.18(2H, br s), 2.49(6H, s), 2.32(6H, s), 2.17(6H, s), 2.14(6H, s), 2.12(6H, s), 2.01(6H, s)
  (5) ¹³C-NMR spectrum: (100 MHz, in CDCl₃) δ(ppm): 188.6, 170.6, 161.1, 157.8, 154.6, 143.7, 138.7, 133.5, 124.1, 121.2, 115.5, 114.9, 107.6, 104.6, 19.1, 16.7, 12.0, 11.9, 9.8, 8.0
  (6) Mass spectrum: (SIMS) m/z: 779(M+1)⁺

(7) Color reaction: positive in each of iodine, 50% sulfuric acid, anisaldehyde and nitroprusside reactions; and negative in each of anilinephthalic acid, ninhydrin and Rydon-Smith reactions (8) Solubility: soluble in methanol, ethanol, acetone, ethyl acetate, acetonitrile, dimethylsulfoxide and chloroform; and insoluble in hexane and water 2. KS-506x (1) Appearance: white powder (2) Molecular formula: $C_{39}H_{42}O_{11}S_2$ (3) Infrared absorption spectrum: (KBr tablet) $cm^{-1}$: 3470, 1645, 1613, 1588, 1452, 1280, 1214, 1166, 1100, 790

(4) $^1$H-NMR spectrum: (400 MHz, in $CD_3OD$) δ(ppm): 2.61(3H, br s), 2.49(3H, br s), 2.16 (6H, s), 2.12(3H, s), 2.084(3H, s), 2.080(3H, s), 2.03(3H, s), 1.89(3H, s), 2.1–1.8(9H)

(5) $^{13}$C-NMR spectrum (100 MHz, in $CD_3OD$) δ(ppm): 194.2, 172.0, 171.8, 162.3, 161.8, 160.7, 160.4, 157.1, 157.0, 150.9, 145.0, 141.5, 139.3, 139.1, 133.4, 124.9, 123.6, 123.2, 118.5, 117.8(2), 117.2, 117.0, 109.7, 109.5, 105.6, 104.4, 19.8, 19.1, 18.8, 16.6, 13.2, 12.51, 12.49, 12.3, 10.7, 10.2, 8.72, 8.66

(6) Mass spectrum: (SIMS) m/z: 751(M+1)$^+$ (7) Color reaction: positive in each of iodine, 50% sulfuric acid, anisaldehyde and nitroprusside reactions; and negative in each of anilinephthalic acid, ninhydrin and Rydon-Smith reactions (8) Solubility: soluble in methanol, ethanol, acetone, ethyl acetate, acetonitrile, dimethylsulfoxide and chloroform; and insoluble in hexane and water 3. KS-506g (1) Appearance: white powder (2) Molecular formula: $C_{38}H_{42}O_{10}S_2$ (3) Infrared absorption spectrum: (the solution method, in $CHCl_3$) $cm^{-1}$: 3620, 3420, 1650, 1615, 1590, 1450, 1320, 1280, 1170

(4) $^1$H-NMR spectrum: (400 MHz, in DMSO-$d_6$, 343° K.) δ(ppm): 10.69(1H, s), 8.83(1H, s), 8.70(1H, s), 2.25(3H, s), 2.09(6H, s), 2.07(6H, s), 1.96(3H, s)

(5) $^{13}$C-NMR spectrum (25 MHz, in $CD_3OD$) δ(ppm): 171.9, 161.5, 160.1, 156.7, 150.4, 141.6, 139.1, 123.3, 120.1, 117.4, 116.6, 109.5, 105.5, 19.0, 18.2, 13.2, 12.5, 10.9, 8.7

(6) Mass spectrum: (SIMS) m/z: 723(M+1)$^+$ (7) Color reaction: positive in each of iodine, 50% sulfuric acid, anisaldehyde and nitroprusside reactions; and negative in each of anilinephthalic acid, ninhydrin and Rydon-Smith reactions (8) Solubility: soluble in methanol, ethanol, acetone, ethyl acetate, acetonitrile, dimethylsulfoxide and chloroform; and insoluble in hexane and water 4. KS-506m (1) Appearance: glassy solid (2) Molecular formula: $C_{24}H_{28}O_7S$ (3) Infrared absorption spectrum: (the solution method, in $CHCl_3$) $cm^{-1}$: 3630, 3400, 1715, 1665, 1615, 1585, 1460, 1313, 1170, 1104

(4) $^1$H-NMR spectrum: (400 MHz, in $CDCl_3$) δ(ppm): 11.41(1H, s), 5.44(1H, br s), 5.17(1H, br s), 3.06(2H, br t), 2.52(2H, br t), 2.55(3H, s), 2.21(3H, s), 2.19(3H, s), 2.154(3H, s), 2.146(3H, s), 2.04(3H, s), 1.93(3H, s)

(5)$^{13}$C-NMR spectrum: (100 MHz, in $CDCl_3$) δ(ppm): 206.2, 194.7, 170.4, 161.1, 157.9, 153.9, 143.4, 138.4, 132.3, 126.4, 121.0, 115.5, 114.9, 107.7, 104.9, 43.0, 29.4, 23.6, 19.2, 16.6, 12.1, 11.9, 9.9, 8.1

(6) Mass spectrum: (HRMS) Found: 460.1540 Calculated for $C_{24}H_{28}O_7S$: 460.1553

(7) Color reaction: positive in each of iodine, 50% sulfuric acid, anisaldehyde and nitroprusside reactions; and negative in each of anilinephthalic acid, ninhydrin and Rydon-Smith reactions (8) Solubility: soluble in methanol, acetone, ethyl acetate, acetonitrile and dimethylsulfoxide; and insoluble in hexane and water 5. KS-506h (1) Appearance: colorless powder (2) Molecular formula: $C_{21}H_{24}O_7$ (3) Infrared absorption spectrum: (the solution method, in $CHCl_3$) $cm^{-1}$: 3630, 3400, 1723, 1654, 1618, 1588, 1460, 1433, 1314, 1278, 1168, 1113, 1094

(4) $^1$H-NMR spectrum: (400 MHz, in $CDCl_3$) δ(ppm): 11.36(1H, s), 5.28(1H, br s), 5.01(1H, br s), 3.69(3H, s), 2.55(3H, s), 2.28(3H, s), 2.19(6H, s), 2.16(3H, s), 2.06(3H, s)

(5) $^{13}$C-NMR spectrum: (100 MHz, in $CDCl_3$) δ(ppm): 170.5, 168.0, 160.8, 157.7, 153.9, 145.0, 138.3, 134.4, 120.8, 120.0, 115.4, 114.7, 107.7, 105.1, 52.2, 18.9, 17.3, 12.0(2), 9.8, 8.1

(6) Mass spectrum: (HRMS) Found: 388.1518 Calculated for $C_{21}H_{24}O_7$: 388.1520

(7) Color reaction: positive in each of iodine, 50% sulfuric acid and anisaldehyde reactions; and negative in each of aniline-phthalic acid, ninhydrin, Rydon-Smith and nitroprusside reactions (8) Solubility: soluble in methanol, acetone, ethyl acetate, acetonitrile and dimethylsulfoxide; and insoluble in hexane and water The $R_f$ values in thin layer chromatography of KS-506 compounds with various developers are indicated in Table 1. Detection was carried out by spraying 50% sulfuric acid followed by heating on a hot plate.

TABLE 1

| Developer | $R_f$ value | | | | |
|---|---|---|---|---|---|
| | KS-506a | KS-506x | KS-506g | KS-506m | KS-506h |
| (1) Chloroform:methanol = 9:1 (v/v) | 0.38 | 0.38 | 0.38 | 0.47 | 0.46 |
| (2) n-hexane:ethyl acetate = 1:1 (v/v) | 0.50 | 0.50 | 0.50 | 0.32 | 0.41 |
| (3) methanol:water = 8:2 (v/v) | 0.21 | 0.21 | 0.21 | 0.38 | 0.35 |
| (4) acetonitrile:water = 8:2 (v/v) | 0.50 | 0.50 | 0.50 | | |
| acetonitrile:water = 7:3 (v/v) | | | | 0.42 | 0.48 |

Note:
Thin layer:
(1), (2): Silica gel 60 $F_{254}$ plate (Merck Inc., No. 5628)
(3), (4): RP-8$F_{254s}$ plate (Merck Inc., No. 13725)
Development: room temperature, the ascending method, 10 to 30 minutes The PDE-inhibiting activity of KS-506a, KS-506x and KS-506g is shown below by Experimental Example 1.

EXPERIMENTAL EXAMPLE 1

A PDE preparation partially purified from bovine cerebral cortex according to the method of Kakiuchi, et al. (Biochem J., 146, 109–120 (1975)) was used as the PDE in the experiment. Methanol solutions of the test compounds at various concentrations (50 μl each) were respectively added to 500 μl of a reaction mixture comprising 80 mM imidazole-hydrochloride buffer (pH 6.9), 3 mM magnesium sulfate, 0.3 mM dithiothreitol, 100 mM sodium chloride, 50 μM calcium chloride, 1.2 mM cAMP, 4 U/ml calmodulin (1U is defined as the amount which activates 50% of the maximum activity of PDE under the conditions) and 26 mU/ml PDE (1U is defined as the amount which hydrolyzes 1 μmol of cAMP in one minute), and reaction was allowed to proceed at 30° C. for 30 minutes.

The reaction was discontinued by heating at 100° C. for 5 minutes. Then, 6 μmol of manganese chloride and 0.2 U of 5'-nucleotidase (1U is defined as the amount which forms 1 μmol of phosphoric acid in one minute) were added to the reaction mixture, and reaction was allowed to proceed at 30° C. for 30 minutes. The reaction was discontinued by addition of 3 ml of 10% perchloric acid, and the formed inorganic phosphoric acid was quantitatively determined according to the method of Ames (Method in Enzymology 8, 115-116, 1966, Academic Press). Inhibition rate was calculated in accordance with the following equation:

$$\text{Inhibition rate} = (A - B)/A \times 100 \ (\%)$$

A: Amount of the inorganic phosphoric acid formed in the absence of a test compound
B: Amount of the inorganic phosphoric acid formed in the presence of a test compound The concentration of a test compound inhibiting 50% of the PDE activity is indicated as $IC_{50}$ in Table 2.

TABLE 2

| Test compound | $IC_{50}$ (μg/ml) |
|---|---|
| KS-506a | 1.22 |
| KS-506x | 0.28 |
| KS-506g | 0.080 |
| Papaverine hydrochloride | 60 |
| Reticurol | 20 |

The activity of KS-506m and KS-506h to inhibit histamine release is shown below by Experimental Example 2.

EXPERIMENTAL EXAMPLE 2

Effect on Histamine Release from Rat Peritoneal Exudate Cells

1) Preparation of Suspension of Rat Abdominal Cavity Cells and Effect on Histamine Release Rats weighing from 350 to 450 g were sacrificed by exsanguination under dry ether anesthesia, and a medium for mast cells (composition : 150 mM NaCl, 3.7 mM KCl, 3 mM $Na_2HPO_4$, 3.5 mM $KH_2PO_4$, 1 mM $CaCl_2$, 5.6 mM glucose, 0.1% bovine serum albumin and 10 U/ml heparin) prepared according to the method of Sullivan, et al. [J. Immunol. 114, 1473 (1973)] was intraperitoneally injected into the animals in an amount of 15 ml/animal. After massage of the abdominal parts for 2 minutes, the animals were subjected to celiotomy to sample exudate in the abdominal cavities. The collected exudate was subjected to centrifugation at 100 xg at 4° C. for 5 minutes, and the precipitate was mixed with an appropriate amount of the ice-cooled medium for mast cells mentioned above to prepare a suspension. Then, the centrifugation and the addition of the medium were repeated three times to prepare a cell suspension wherein the final concentration of the mast cells was about $2 \times 10^5$ cells/ml. Identification of the mast cells was carried out by staining intracellular granules with 0.05% Toluidine Blue.

One milliliter portions of the thus obtained cell suspension were preincubated at 37° C. for 5 minutes, and then respectively mixed with 0.1 ml each of test compound solutions having various concentrations, followed by incubation for 5 minutes. The incubated mixtures were further mixed with 0.1 ml each of 10 μg/ml phosphatidyl-L-serine and concanavalin A, and then incubated for 15 minutes.

Spontaneous histamine release was determined under similar incubation conditions except that physiological saline was used in place of phosphatidyl-L-serine and concanavalin A.

The reaction was stopped by addition of 3 ml of ice-cooled physiological saline, and the cell suspension was subjected to centrifugation at 1100 xg at 4° C. for 10 minutes to obtain a supernatant and a residue. Histamine contents of the supernatant and the residue were measured by the fluorescence method according to the method of Komatsu [Allergy 27, 67 (1978)]. Histamine release rate was indicated as the percentage of the histamine content of the supernatant to the total histamine content of the cells. The rate of inhibition of histamine release by the test compound solution was calculated according to the following equation:

$$\text{Release inhibition rate (\%)} = \left[ 1 - \frac{\text{Histamine realease rate in the presence of a test compound} - \text{Spontaneous release rate}}{\text{Histamine realease rate in the absence of a test compound} - \text{Spontaneous release rate}} \right] \times 100$$

2) Experimental Results

TABLE 3

| | Concentration of test compound (μg/ml) | Release inhibition rate (%) | $IC_{50}$* (μg/ml) |
|---|---|---|---|
| KS-506m | 0.5 | 27.9 | 1.2 |
| | 1.5 | 58.4 | |
| | 5.0 | 83.3 | |
| KS-506h | 3.0 | 13.9 | 8.2 |
| | 10.0 | 59.9 | |

*the concentration of a test compound which inhibits histamine release by 50%.

The process for producing KS-506 compounds is explained below.

KS-506 compounds are prepared by culturing a microorganism which belongs to the genus Mortierella and which has an ability to produce KS-506 compounds in a medium, allowing KS-506 compounds to accumulate in the culture, mainly in the cells, and recovering KS-506 compounds from the culture.

As the KS-506 compound-producing strain, any strain may be used so long as it belongs to the genus Mortierella and has an ability to produce at least one member selected from KS-506 compounds. A specific example of a suitable strain is *Mortierella vinacea* KAC-1436 strain (hereinafter referred to as KAC-1436) which was isolated by the present inventors from fallen branches of a Japanese beech in Nagano Prefecture.

The mycological characteristics of KAC-1436 are as follows.

When KAC-1436 is cultured in malt extract agar medium at 25° C., a diameter of a colony reaches 35 to 40 mm on the 7th day from the start of the culturing. The colonies are gray at first and become reddish with lapse of the culture period. The result of observation with an optical microscope indicates that the hyphae of the strain elongate and branch well on and in a medium, but lack such distinct septum formation as is observed in Ascomycota, Basidiomycota and Deuteromycotina. The sporangiophores are formed mainly from the aerial hyphae, and have a length of 100 μm and a width of 2.5 to 4.5 μm. The sporangia are spherical or sphere-like, smooth, and 12 to 13.5 μm in diameter, and lack columella. Many non-motile sporangiospores are formed in the sporangia. The sporangiospores are non-regular polygonal, smooth and 2 to 4 μm. No zygospore is observed.

As a result of the above observations, the strain was identified as *Mortierella vinacea*. The mycological characteristics of *Mortierella vinacea* are detailedly described on page 163 of H. Zycha, et al., "Mucorales" (Cramer, 1969). The present inventors designated the above strain *Mortierella vinacea* KAC-1436, which was deposited with the Fermentation Research Institute, Agency of Industrial Science and Technology on Mar. 2, 1988 as FERM BP-1776.

For the culturing of the strain, ordinary culture methods used for the culturing of fungi may be used. As the medium, either a natural medium or a synthetic medium may be used so long as it properly contains carbon sources, nitrogen sources, inorganic substances and the like which may be assimilated by the strain.

As the carbon source, carbohydrates such as glucose, fructose, stabirose, saccharose, lactose, starch, dextrin, mannose, maltose, molasses and instant mashed potato; organic acids such as citric acid, malic acid, acetic acid and fumaric acid; amino acids such as glutamic acid; glycerol, cottonseed oil, etc. can be used.

As the nitrogen source, ammonium salts such as ammonium chloride, ammonium sulfate, ammonium nitrate and ammonium phosphate; amino acids such as aspartic acid, glutamine, cystine and alanine; urea, malt extract, peptone, meat extract, yeast extract, dry yeast, corn steep liquor, soybean powder, cottonseed cake, soybean casein, Casamino acid, Pharmamedia, soluble vegetable protein, vegetable or fruit juice, etc. can be used.

As the inorganic substances, potassium dihydrogen phosphate, disodium hydrogen phosphate, magnesium sulfate, ferrous sulfate, manganese sulfate, cobalt sulfate, zinc sulfate, calcium pantothenate, ammonium molybdate, potassium aluminum sulfate, barium carbonate, calcium carbonate, cobalt chloride, sodium chloride, magnesium phosphate, etc. can be used.

Further, substances which promote the growth of the cells or the production of KS-506 compounds, for example, vitamins such as thiamine may be added to the medium, if necessary.

When the microorganism to be used requires a particular substance for its growth, it is necessary to add such a substance.

Culturing is carried out at a temperature of 15° to 30° C. at pH around neutrality by shaking culture, aeration-stirring culture, etc.

By culturing for 5 to 12 days, accumulation of KS-506 compounds reaches a maximum and the culturing is completed.

For isolation and recovery of the accumulated KS-506 compounds from the cells, conventional methods for recovering physiologically active substances from cells may be employed.

That is, KS-506 compounds can be isolated by separation of the cells by filtration, centrifugation, etc.; extraction from the cells with an organic solvent such as methanol or acetone; partition with water or at least two organic solvents; adsorption and desorption treatments of the active substances by column chromatography or thin layer chromatography using an adsorptive resin, silica gel, a chemically modified silica gel, aluminum, cellulose, diatomaceous earth, magnesium silicate, a gel filtering agent, etc.; or the like.

An example of the process for isolating KS-506 compounds from the cells is given below.

The cells are separated from the culture by filtration or centrifugation. An organic solvent such as methanol is added to the obtained cells, followed by adequate stirring. By further filtration or centrifugation, the cells and the filtrate or supernatant are separated. The filtrate or supernatant is concentrated by evaporating the solvent under reduced pressure to obtain an aqueous solution. Extraction from this aqueous solution is carried out using a suitable water-immiscible solvent such as ethyl acetate. The extract is concentrated under reduced pressure, and the concentrate is repeatedly subjected to silica gel column chromatography using a solvent mixture such as chloroform-methanol or water-acetonitrile as a developing solvent.

Then, the fractions containing KS-506 compounds are combined and concentrated under reduced pressure, and the resulting residue is repeatedly subjected to Sephadex LH-20 column chromatography using methanol as a developing solvent. The fractions containing KS-506 compounds are combined and concentrated under reduced pressure to obtain KS-506 compounds as white powder.

Detection of KS-506 compounds during the above purification steps is carried out by silica gel thin layer chromatography, followed by spraying of 50% sulfuric acid and heating.

Further, if desired, KS-506h may also be prepared by heating KS-506a in basic methanol. KS-506m may also be prepared, if desired, by heating KS-506a under reflux in the presence of methyl vinyl ketone.

Certain specific embodiments of the present invention are illustrated by the following examples.

EXAMPLE 1

KAC-1436 was used as the seed strain. The strain was inoculated into 30 ml of a seed medium (pH 6.0) having the composition of 1.0 g/dl glucose, 0.5 g/dl peptone (Kyokuto Pharmaceutical Industry Co., Ltd.), 0.5 g/dl dry yeast Ebios (Asahi Breweries, Ltd.), 0.2 dl/dl V-8 Vegetable Juice (Campbell Soup Co.) and 0.3 g/dl calcium carbonate in a 300 ml-Erlenmeyer flask, and subjected to shaking culture at 25° C. until the cells sufficiently grew. The whole seed culture was inoculated into 300 ml of a seed medium having the same composition as above in a 2 l-Erlenmeyer flask, and similarly cultured. Then, 1800 ml of the resulting seed culture was inoculated into 18 l of a fermentation medium (pH 7.0) having the composition of 0.5 g/dl glucose, 4 g/dl maltose, 1 g/dl 3-(N-morpholino) propanesulfonic acid, 0.05 g/dl magnesium sulfate heptahydrate, 1.5 g/dl soybean meal, 1.5 g/dl Pharmamedia and 0.5 g/dl calcium carbonate in a 30 l-jar fermenter.

Culturing was carried out at 25° C. for 10 days with aeration and stirring (aeration: 18 l/min, rotation : 300 rpm). After the completion of the culturing, 30 l of the culture was filtered using a filter aid to separate it into the cells and the culture supernatant. To the cells was added 20 of methanol, followed by thorough stirring to extract KS-506a, KS-506x and KS-506g. The methanol extract of the cells was concentrated under reduced pressure to remove methanol. To the resulting aqueous solution was added methanol to 5% (v/v), and the mixture was passed through a column packed with 2 l of Diaion HP-20 (Mitsubishi Kasei Corporation) equilibrated with water in advance. After the column was washed with 6 l of water and then with 6 l of an aqueous 50% methanol solution, KS-506a, KS-506x and KS-506g were eluted with 10 l of methanol. The eluate was concentrated under reduced pressure, and the concentrate was mixed with silica gel (Wako Gel C-200, Wako Pure Chemical Industries, Ltd.) and supplied to the top of 1 l of silica gel (Wako Gel C-200) packed in a column in advance using chloroform:methanol = 9:1 (v/v). Elution of KS-506a, KS-506x and KS-506g was carried out with 5 l of chloroform:methanol = 9:1 (v/v). The eluate was concentrated under reduced pressure, and the residue was dissolved in 10 ml of chloroform containing 1% methanol. The solution was supplied to the top of 1 l of silica gel (Wako Gel C-200) packed in a column in advance using 1% methanol-chloroform. Development was carried out successively with 2 l each of chloroform containing 1%, 2% and 3% methanol, respectively, and the eluate was taken in 20 ml portions. KS-506a, KS-506x and KS-506g were eluted in fractions Nos. 101 to 181. These fractions were combined and concentrated under reduced pressure to obtain 1.0 g of a light yellow syrupy substance. The syrupy substance was dissolved in 2 ml of an aqueous 80% acetonitrile solution, and one half of the resulting solution was supplied to a reversed phase Lobar column (Merck Inc., RP-8, size B) packed in advance with an aqueous 80% acetonitrile solution. Elution was carried out with an aqueous 80% acetonitrile solution and the eluate was taken in 5 ml portions. KS-506a, KS-506x and KS-506g were eluted in fractions Nos. 56 to 86. The remaining half of the solution of the syrupy substance was similarly subjected to reversed phase Lobar column chromatography, and the fractions containing KS-506a, KS-506x and KS-506g were combined. The fractions containing KS-506a, KS-506x and KS-506g were concentrated under reduced pressure, and the residue was dissolved in 1 ml of methanol. The solution was supplied to the top of 200 ml of Sephadex LH-20 (Pharmacia Fine Chemicals Inc.) packed in a column in advance with methanol, followed by development with 1 l of methanol. The eluate was taken in 5 ml portions, and KS-506a, KS-506x and KS-506g were eluted in fractions Nos. 51 to 61. The fractions containing KS-506a, KS-506x and KS-506g were combined, concentrated under reduced pressure, and subjected to Sephadex LH-20 column chromatography again, whereby 450 mg of fractions containing KS-506a, KS-506x and KS-506g were obtained. Then, 42 mg of the fractions was dissolved in 1 ml of an aqueous 60% acetonitrile solution, and the solution was supplied to a reversed phase Lobar column (Merck Inc. RP-18, size B) packed in advance with an aqueous 60% acetonitrile solution, and subjected to high performance liquid chromatography with monitoring. Elution was carried out with 2 l of an aqueous 60% acetonitrile solution, and the eluate was taken in 10 ml portions. Fractions Nos. 101 to 117, 122 to 128 and 132 to 150 were combined respectively and concentrated under reduced pressure to obtain 19.6 mg of KS-506x, 6.9 mg of KS-506g and 7.8 mg of KS-506a, respectively, as white powder.

EXAMPLE 2

KAC-1436 was cultured in the same manner as in Example 1.

After the completion of the culturing, 30 l of the culture was filtered using a filter aid to separate it into the cells and the culture supernatant. To the cells was added 20 l of methanol, followed by thorough stirring to extract KS-506m and KS-506h. The methanol extract of the cells was concentrated under reduced pressure to remove methanol. To the resulting aqueous solution was added methanol to 5% (v/v), and the mixture was passed through a column packed with 2 l of Diaion HP-20 equilibrated with water in advance. After the column was washed with 6 l of water and then with 6 l of an aqueous 50% methanol solution, KS-506m and KS-506h were eluted with 10 l of methanol. The eluate was concentrated under reduced pressure, and the concentrate was mixed with silica gel (Wako Gel C-200) and supplied to the top of 1 l of silica gel (Wako Gel C-200) packed in a column in advance using chloroform:methanol = 9:1 (v/v). Elution of KS-506m and KS-506h was carried out with 5 l of chloroform:methanol = 9:1 (v/v). The eluate was concentrated under reduced pressure, and the residue was dissolved in 10 ml of chloroform containing 1% methanol. The solution was supplied to the top of 1 l of silica gel (Wako Gel C-200) packed in a column in advance using 1% methanolchloroform. Development was carried out successively with 2 l each of chloroform containing 1%, 2% and 3% methanol, respectively, and the fractions containing KS-506m and those containing KS-506h were respectively combined and concentrated under reduced pressure.

These fractions were respectively mixed with silica gel (Wako Gel C-200) and supplied to the top of 300 ml of the same silica gel packed in a column in advance using 10% ethyl acetate-n-hexane. Development was carried out successively with 10%, 20%, 30% and 40% ethyl acetate-n-hexane solutions. First, KS-506h was eluted and then KS-506m was eluted. The fractions containing each of the substances alone were respectively combined and concentrated under reduced pressure to obtain 80 mg of KS-506m as glassy solid and 120 mg of KS-506h as colorless powder.

Detection of KS-506m and KS-506h during the above purification steps was carried out by thin layer chromatography using a silica gel plate (Silica Gel 60 $F_{254}$, Merck Inc.) followed by spraying of 50% sulfuric acid and heating on a hot plate.

EXAMPLE 3

KS-506a (230 mg) obtained in Example 1 was dissolved in 230 ml of methanol, and 23 ml of an aqueous 1N sodium hydroxide solution was added to the solution, followed by heating at 60° C. for 30 minutes. After the completion of the reaction, the mixture was neutralized with 1N hydrochloric acid and then concentrated to dryness under reduced pressure. The resulting solid was mixed with silica gel (Wako Gel C-300, Wako Pure Chemical Industries, Ltd.) and supplied to the top of 500 ml of silica gel (Wako Gel C-300) packed in a column in advance using 10% ethyl acetate-n-hexane. Elution was carried out successively with 2 l each of 10%, 20%, 30% and 40% ethyl acetate-n-hexane. The eluate was taken in 15 ml portions, and the fractions containing KS-506h were combined and concentrated to dryness to obtain 60 mg of KS-506h as colorless powder.

EXAMPLE 4

To 3 mg of KS-506a obtained in Example 1, was added 0.5 ml of methyl vinyl ketone, and the mixture was heated at 60° C. for 15 hours. After the completion of the reaction, the mixture was concentrated to dryness, and the residue was subjected to thin layer chromatography using a silica gel plate (Silica Gel 60 F$_{254}$) and chloroform:methanol=20:1 (v/v) as a developing solvent. KS-506m was detected by ultraviolet irradiation at 254 nm, and the part of the silica gel where KS-506m was detected was scraped and subjected to elution with 20 ml of methanol. The methanol eluate was concentrated to dryness under reduced pressure to obtain 2 mg of KS-506m.

What is claimed is:

1. A compound of the formula

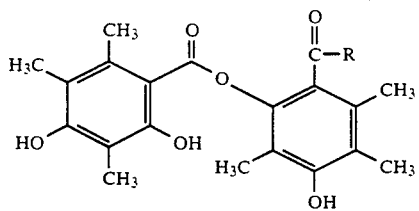

wherein

$R = -OCH_3$.